United States Patent [19]

Collins

[11] 4,000,289
[45] Dec. 28, 1976

[54] ANIMAL FEED AND PROCESS

[75] Inventor: Robert J. Collins, Portage, Mich.

[73] Assignee: The Upjohn Company, Kalamazoo, Mich.

[22] Filed: July 8, 1971

[21] Appl. No.: 160,950

[52] U.S. Cl. ............................................. 424/269
[51] Int. Cl.² ..................................... A61K 31/41
[58] Field of Search ......................... 424/244, 269

[56] References Cited

UNITED STATES PATENTS 3,577,553   5/1971   Ferlauto .......................... 424/269

FOREIGN PATENTS OR APPLICATIONS 2,012,190   9/1970   Germany ......................... 424/244
916,543     5/1970   Netherlands ..................... 424/244

Primary Examiner—Frederick E. Waddell
Attorney, Agent, or Firm—John J. Killinger; Roman Saliwanchik

[57] ABSTRACT

An animal feed comprising a compound of the group consisting of 6-phenyl-4H-s-triazolo[4,3-a][1,4]benzodiazepines of the formula:

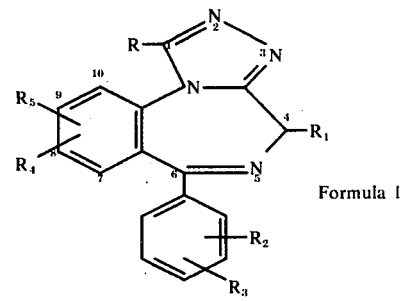

Formula I wherein R is selected from the group consisting of hydrogen, alkyl of 1 to 3 carbon atoms, inclusive, phenyl, benzyl and -COOR' in which R' is alkyl of 1 to 4 carbon atoms, inclusive; wherein $R_1$ is selected from the group consisting of hydrogen and alkyl of 1 to 3 carbon atoms, inclusive; and wherein $R_2$, $R_3$, $R_4$ and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atom, inclusive and their pharmacologically acceptable acid addition salts in combination with a nutrient feed. A process for obtaining increased productivity in meat producing, milk producing, and egg laying animals by feeding the aforementioned compounds in combination with nutrient feeds.

6 Claims, No Drawings

1

ANIMAL FEED AND PROCESS

CROSS REFERENCE TO RELATED APPLICATIONS

This application is related to copending United States application Ser. No. 872,394, filed Oct. 29, 1969, which discloses compounds of the formula 1 and methods for their preparation. The aforementioned application has issued as Belgian patent No. 747,493 issued Sept. 17, 1970.

BRIEF SUMMARY OF THE INVENTION

Broadly the present invention encompasses a nutritionally adequate animal feed having dispersed therein a compound of the formula 1 in sufficient concentration to provide increased productivity and feed efficiencies in healthy meat producing, milk producing, or egg laying animals. The invention also includes the process of feeding the composition to meat producing, milk producing, or egg laying animals.

DETAILED DESCRIPTION

It has been found in recent years that meatproducing animals will gain more weight and gain it faster when various classes of compounds such as vitamins, minerals, estrogens, antibiotics, and tranquilizers are added to the diet. Although the presently available compounds are useful, new materials are still being sought that would produce weight gains more rapidly, to a greater extent, more efficiently with respect to feed intake at a lower cost and without undesirable side effects.

It is now possible by use of the present invention to obtain unexpected results in the feeding of meat producing, milk producing, or egg laying animals; that is to say, an increased rate of weight gain, an increased amount of weight gain, an increase in milk production, or increased rate of egg laying, as well as increased feed efficiency can be obtained by the addition of minute quantities of a compound of the Formula 1 to the animals usual nutrient feed.

Compounds of the Formula 1 can be prepared by methods disclosed in United States application Ser. No. 872,394, filed Oct. 29, 1969, and Belgian Patent No. 747,493 issued Sept. 17, 1970.

Unless otherwise specified, all percentages are given on a weight-to-weight basis. The pound (lb.) weights given are avoirdupois units.

Feeding of the compositions of the present invention can commence for birds shortly after hatching and in the case of mammals, during the creep-feeding period of suckling animals when they are starting on solid food and, of course, after weaning. Feeding of the compositions is continued throughout the growing period, lactation period, or egg laying period.

The total concentration of the compound of the Formula 1 in the feed composition is determined with regard to the species of animal, age, weight, and average amount of feed consumed daily. Preferably the compound of the Formula 1 is employed in the finished feed that will supply the animal with a daily intake of from about 0.003 mg. to about 50 mg. per head per day. The following table illustrates the range of compound of Formula 1 in milligrams daily dose per head per day for representative animals.

| Animal | Range Daily Dose/Head, mg. | Preferred Daily Dose, mg |
|---|---|---|
| Swine (birth to 8 weeks) | 0.025 – 2.5 | .14 |
| Swine (40 to 200 lb.) | 0.145 – 14.5 | .8 |
| Chickens (growing 0–8 weeks) | 0.003 – 0.3 | .02 |
| Hens (laying) | 0.006 – 0.6 | .03 |
| Turkeys (growing 0–24 weeks) | 0.02 – 1.0 | .05 |
| Beef Cattle (fattening) | 0.5 – 50. | 2.8 |
| Calves (0–12 weeks) | 0.06 – 6.0 | 0.3 |
| Dairy Cattle (lactation) | 0.5 – 50. | 2.8 |
| Lambs (fattening) | 0.038 – 3.8 | 0.2 |

The foregoing dosage can generally be accomplished by providing from about 25 mg. to about 2500 mg. of a compound of the Formula 1 per ton of finished feed.

Advantageously a compound of the Formula 1 is supplied in the form of a liquid or solid premix wherein the concentration is 100 – 2000 times greater than the desired final concentration of the feed. For example, the compound of Formula 1 can be dissolved or suspended in a fluid vehicle such as corn oil, cottonseed oil, molasses, distillers solubles and the like to prepare a fluid premix. Alternatively, a solid premix can be prepared by mixing a compound of the Formula 1 with an edible solid diluent such as sucrose, lactose, starch, corn meal, flour, calcium carbonate, soybean meal and the like.

EXAMPLE 1

A swine diet for growing hogs of 40 to 100 pounds body weight is prepared from the following types and amounts of ingredients:

| | |
|---|---|
| Corn, ground | 78.15% |
| Soybean oil meal, 44% | 17.0 % |
| Meat and bone scraps, 50% | 3.0 % |
| Oyster shell flour | 0.4 % |
| Bone Meal | 0.5 % |
| Salt | 0.5 % |
| Trace mineral mixture[1] | 0.05% |
| Zinc oxide | 0.01% |
| Vitamin A and D supplement[2] | 0.22% |
| B Vitamin supplement[3] | 0.04% |
| Vitamin $B_{12}$ supplement[4] | 0.08% |

[1]Contains the following % of minerals: Mn, 12; Co, 0.08; Fe, 5.0; Cu, 0.4; I, 0.24; Zn, 0.7.
[2]Contains 300 USP units $D_3$/Gm. and 1500 I.U.A./Gm.
[3]Contains per lb.: riboflavin, 2000 mg.; calcium pantothenate, 4000 mg.; niacin, 9000 mg.; and choline chloride 10,000 mg.
[4]Contains 6 mg. Vitamin $B_{12}$ per lb.

To 999 parts of the preceding feed is added 1 part of a premix composition prepared by mixing .15 gm. of 8-chloro-6-(o-chlorophenyl)-1-methyl-4H-s-triazolo[4,3-a]-[1,4]benzodiazepine with sufficient ground limestone to make one pound.

The feeding composition so prepared supplies 0.15 mg. of 8-chloro-6-(o-chlorophenyl)-1-methyl-4H-s-triazolo-[4,3-a][1,4]benzodiazepine per pound, or about 0.33 parts per million.

The foregoing composition is usefully fed to hogs for increased rate of weight gain and improved utilization of feed.

EXAMPLE 2

A fattening feed for 800 pound yearling cattle is prepared from the following types and amounts of ingredients:

| | |
|---|---|
| Ground ear corn | 89.75% |
| Soybean oil meal, 44% | 9.0 % |
| Ground limestone | 0.7 % |
| Salt | 0.5 % |
| Trace mineral mixture[1] | 0.05% |

[1]Contains the following percent of minerals: Mn, 12; Co, 0.08; Fe, 5.0; Cu, 0.4; I, 0.24; Zn, 0.7.

To 999 parts of the preceding feed is added 1 part of a premix composition prepared by mixing .3 gm. of 8-chloro-6-(o-chlorophenyl)-1-methyl-4H-s-triazolo[4,3-a][1,4]benzodiazepine with sufficient wheat flour to make 1 pound.

The feeding composition so prepared supplies 0.3 mg. of 8-chloro-6-(o-chlorophenyl)-1-methyl-4H-s-triazolo[4,3-a][1,4]benzodiazepine per pound, or about 0.66 parts per million.

Cattle are to receive the foregoing feed ad libitum together with 5 lb. of hay per head per day and when so fed have an increased rate of weight gain and improved utilization of feed.

EXAMPLE 3

A chicken feed for broilers is prepared from the following types and amounts of ingredients:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | .34% |
| 25% Choline chloride | .13% |
| Vitamin B$_{12}$ supplement (6mg./lb.) | .10% |
| Manganese sulfate | .02% |
| Supplemental vitamin mix[1] | .06% |

[1]Consisting of 16.0 gm. Vitamin A supplement (10 units/mg.); 3.6 gm. Vitamin D$_3$ supplement (15,000 units/gm.); 7.1 gm. riboflavin supplement (1 gm. riboflavin per ounce); 500 mg. niacin.

To 999 parts of the preceding feed is added 1 part of a premix composition prepared by mixing .2 gm. of 8-chloro-6-(o-chlorophenyl)-1-methyl-4H-s-triazolo[4,3-a]-[1,4]benzodiazepine with sufficient soybean mill feed to make 1 pound.

The feeding composition so prepared supplies .2 mg. of 8-chloro-6-(o-chlorophenyl)-1-methyl-4H-s-triazolo-[4,3-a][1,4]benzodiazepine per pound, or about 0.44 parts per million.

The foregoing composition is usefully fed to chickens for increased rate of weight gain and improved utilization of feed. Similarly the composition can be fed to turkeys, ducks and geese.

EXAMPLE 4

A diet for fattening lambs is prepared from the following types and amounts of ingredients:

| | |
|---|---|
| Ground ear corn | 82.05% |
| Alfalfa meal | 10.0 % |
| Soybean oil meal 44% | 7.0 % |
| Ground limestone | 0.3 % |
| Salt | 0.6 % |
| Trace mineral mixture[1] | 0.05% |

[1]Contains the following percent of minerals: Mn, 12; Co, 0.08; Fe, 5.0; Cu, 0.4; I, 0.24; Zn, 0.7.

The above feed to be mixed, pelleted and offered to fattening lambs free-choice in conjunction with hay.

To 999 parts of the preceding feed is added 1 part of a premix composition prepared by mixing .14 gm. of 8-chloro-6-(o-chlorophenyl)-1-methyl-4H-s-triazolo[4,3-a][1,4]benzodiazepine with sufficient corn meal to make one pound.

The feeding composition so prepared supplies .14 mg. of 8-chloro-6-(o-chlorophenyl)-1-methyl-4H-s-triazolo-[4,3-a][1,4]benzodiazepine per pound or .31 parts per million.

The foregoing composition is usefully fed to lambs for increased rate of weight gain and improved utilization of feed.

EXAMPLE 5

Following the procedure of the preceding examples 1 to 4, inclusive, animal feeds are similarly prepared, substituting equimolar amounts of:

8-Chloro-1-methyl-6-phenyl-4H-s-triazolo[4,3-a]-[1,4]benzodiazepine

8-Chloro-1-methyl-6-phenyl-4H-s-triazolo[4,3-a]-[1,4]benzodiazepine

8-Chloro-1-methyl-6-(2,6-difluorophenyl)-4H-s-triazolo[4,3-a][1,4]benzodiazepine 8-Chloro-1-methyl-6-(o-fluorophenyl)-4H-s-triazolo-[4,3-a][1,4]benzodiazepine 1-Methyl-6-phenyl-4H-s-triazolo[4,3-a][1,4]benzodiazepine 8-Chloro-1-propyl-6-phenyl-4H-s-triazolo[4,3-a]-[1,4]benzodiazepine 8-Chloro-1-isopropyl-6-phenyl-4H-s-triazolo[4,3-a]-[1,4]benzodiazepine 8-Chloro-1,6-diphenyl-4H-s-triazolo[4,3-a][1,4]-benzodiazepine 1-Benzyl-8-chloro-6-phenyl-4H-s-triazolo[4,3-a]-[1,4]benzodiazepine 8-Chloro-1-ethyl-6-phenyl-4H-s-triazolo[4,3-a]-[1,4]benzodiazepine 1-Methyl-6-phenyl-8-(trifluoromethyl)-4H-s-triazolo[4,3-a][1,4]benzodiazepine 1-Methyl-8-nitro-6-phenyl-4H-s-triazolo[4,3-a]-[1,4]benzodiazepine Ethyl-8-chloro-6-phenyl-4H-s-triazolo[4,3-a]-[1,4]benzodiazepine-1-carboxylate 8-Ethyl-1-phenyl-6-(o-chlorophenyl)-4H-s-triazolo-[4,3-a][1,4]benzodiazepine 7-Ethylthio-1-methyl-6-(o-bromophenyl)-4H-s-triazolo[4,3-a][1,4]benzodiazepine 10-(Trifluoromethyl)-6-[p-(propionylamino)-phenyl]-4H-s-triazolo[4,3-a][1,4]benzodiazepine 7-Ethylthio-1-ethyl-6-(o-bromophenyl)-4H-s-triazolo-[4,3-a][1,4]benzodiazepine 9-Propoxy-8-bromo-1-benzyl-6-[m-(ethylsulfinyl)-phenyl]-4H-s-triazolo[4,3-a][1,4]benzodiazepine 10-(Dipropylamino)-7-methyl-1-isopropyl-6-[m-(propylsulfonyl)phenyl]-4H-s-triazolo-[4,3-a][1,4]benzodiazepine 9-Cyano-1-propyl-6-[p-(trifluoromethyl)phenyl]-4H-s-triazolo[4,3-a][1,4]benzodiazepine 9-Nitro-1-phenyl-6-(o-chlorophenyl)-4H-s-triazolo-[4,3-a][1,4]benzodiazepine 7,10-Dichloro-1-methyl-6-(p-isopropylphenyl)-4H-s-triazolo[4,3-a][1,4]benzodiazepine 4-Methyl-8-bromo-1-isopropyl-6-(o-fluorophenyl)-4H-s-triazolo[4,3-a][1,4]benzodiazepine 1,4,7,9-Tetramethyl-6-(o-chlorophenyl)-4H-s-triazolo[4,3-a][1,4]benzodiazepine 10-(Propylsulfonyl)-8-methyl-1-ethyl-6-phenyl-4H-s-triazolo[4,3-a][1,4]benzodiazepine 8-(Dimethylamino)-6-phenyl-4H-s-triazolo[4,3-a]-[1,4]benzodiazepine 7,10-Dichloro-1-phenyl-6-(p-isopropylphenyl)-4H-s-triazolo[4,3-a][1,4]benzodiazepine 7,9-Diethyl-1-benzyl-6-(m-ethylphenyl)-4H-s-triazolo[4,3-a][1,4]benzodiazepine 7-Nitro-1-methyl-6-(o-cyanophenyl)-4H-s-triazolo[4,3-a][1,4]benzodiazepine 8-(Dipropylamino)-6-(o-nitrophenyl)-4H-s-triazolo[4,3-a][1,4]benzodiazepine 10-(Acetylamino)-1-ethyl-6-(p-cyanophenyl)-4H-s-triazolo[4,3-a][1,4]benzodiazepine Butyl-8-chloro-6-(m-nitrophenyl)-4H-s-triazolo-[4,3-a][1,4]benzodiazepine-1-carboxylate Methyl-9-fluoro-6-(2,4-dichlorophenyl)-4H-s-triazolo[4,3-a][1,4]benzodiazepine-1-carboxylate 8-Chloro-6-phenyl-4H-s-triazolo[4,3-a][1,4]benzodiazepine 10-Chloro-1-methyl-6-(m-isopropylphenyl)-4H-s-triazolo[4,3-a][1,4]benzodiazepine 9-(dipropylamino)-1-phenyl-6-[p-(propionylamino)-phenyl]-4H-s-triazolo[4,3-a][1,4]benzodiazepine 8-(methylsulfinyl)-1-benzyl-6-(o-nitrophenyl)-4H-s-triazolo[4,3-a][1,4]benzodiazepine 7-(ethylsulfonyl)-1-propyl-6-(o-cyanophenyl)-4H-s-triazolo[4,3-a][1,4]benzodiazepine 4-propyl-1-isopropyl-6-[m-(methylthio)phenyl]-4H-s-triazolo[4,3-a][1,4]benzodiazepine 10-fluoro-7-chloro-1-ethyl-6-[p-(trifluoromethyl)-phenyl]-4H-s-triazolo[4,3-a][1,4]benzodiazepine 7,9-diethoxy-1-methyl-6-(m-ethoxyphenyl)-4H-s-triazolo[4,3-a][1,4]benzodiazepine 7-(propylthio)-6-(m-iodophenyl)-4H-s-triazolo-[4,3-a][1,4]benzodiazepine 8-(acetylamino)-6-(p-iodophenyl)-4H-s-triazolo-[4,3-a][1,4]benzodiazepine 4-propyl-6-(o-iodophenyl)-4H-s-triazolo[4,3-a]-[1,4]benzodiazepine 4-ethyl-1-methyl-6-[o-ethylthio)phenyl]-4H-s-triazolo[4,3-a][1,4]benzodiazepine 4-methyl-7,10-dichloro-1-ethyl-6-(m-isopropoxyphenyl)-4H-s-triazolo[4,3-a][1,4]benzodiazepine 9-(propionylamino)-1-propyl-6-[m-(propylthio)-phenyl]-4H-s-triazolo[4,3-a][1,4]benzodiazepine 7-(diisopropylamino)-1-phenyl-6-[p-(dipropylamino)-phenyl]-4H-s-triazolo[4,3-a][1,4]benzodiazepine 4-isopropyl-7,9-diiodo-1-benzyl-6-phenyl-4H-s-triazolo[4,3-a][1,4]benzodiazepine 8-chloro-1-methyl-6-(3,4-dimethylphenyl)-4H-s-triazolo[4,3-a][1,4]benzodiazepine 6-(2-methyl-4-methoxyphenyl)-4H-s-triazolo[4,3-a]-[1,4]benzodiazepine 8-methylthio-1-methyl-6-phenyl-4H-s-triazolo[4,3-a][1,4]benzodiazepine 8-methoxy-1-methyl-6-phenyl-4H-s-triazolo[4,3-a]-[1,4]benzodiazepine for the 8-chloro-6-(o-chlorophenyl)-1-methyl-4H-s-triazolo[4,3-a][1,4]benzodiazepine of the examples.

I claim:

1. A process for obtaining increased production comprising the feeding of an effective amount of a compound selected from the group consisting of compounds of the formula:

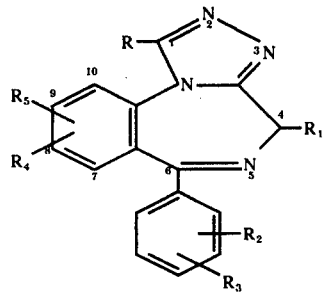

wherein R is selected from the group consisting of hydrogen, alkyl of 1 to 3 carbon atoms, inclusive, phenyl, benzyl and -COOR' in which R' is alkyl of 1 to 4 carbon atoms, inclusive; wherein $R_1$ is selected from the group consisting of hydrogen and alkyl of 1 to 3 carbon atoms, inclusive; and wherein $R_2$, $R_3$, $R_4$ and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive and their pharmacologically acceptable acid addition salts in combination with the nutrient feed to an animal kept for meat, milk or egg production.

2. The process of claim 1 wherein the member selected is in a concentration of from 25 mg. to 2500 mg. per pound of nutrient carrier in the form of a premix.

3. The process of claim 1 wherein the member selected is in the concentration from 25 mg. to 2500 mg. per ton of feed.

4. The process of claim 1 wherein the compound is 8-chloro-1-methyl-6-(o-chlorophenyl)-4H-s-triazolo[4,3-a][1,4]benzodiazepine.

5. The process of claim 2 wherein the compound is 8-chloro-1-methyl-6-(o-chlorophenyl)-4H-s-triazolo[4,3-a][1,4]-benzodiazepine.

6. The process of claim 3 wherein the compound is 8-chloro-1-methyl-6-(o-chlorophenyl)-4H-s-triazolo[4,3-a][1,4]benzodiazepine.

* * * * *